(12) United States Patent
McKenna

(10) Patent No.: US 6,902,320 B2
(45) Date of Patent: Jun. 7, 2005

(54) PATIENT TABLE WITH CANTILEVERED RADIOLUCENT PALLET

(75) Inventor: Gilbert W. McKenna, Revere, MA (US)

(73) Assignee: Analogic Corporation, Peabody, MA (US)

(*) Notice: Subject to any disclaimer, the term of this patent is extended or adjusted under 35 U.S.C. 154(b) by 0 days.

(21) Appl. No.: 10/679,045

(22) Filed: Oct. 3, 2003

(65) Prior Publication Data
US 2004/0131159 A1 Jul. 8, 2004

Related U.S. Application Data

(60) Provisional application No. 60/415,741, filed on Oct. 3, 2002.

(51) Int. Cl.[7] .............................. H05G 1/00; A61B 6/04
(52) U.S. Cl. ............................ 378/208; 378/209; 5/601
(58) Field of Search ................................. 378/208, 209, 378/195, 177; 5/601, 611, 610

(56) References Cited

U.S. PATENT DOCUMENTS

| 4,145,612 A | * | 3/1979 | Cooper .......................... 378/208 |
| 5,450,297 A | * | 9/1995 | Akashi et al. ................. 362/92 |
| 5,499,415 A | | 3/1996 | McKenna |
| 5,613,254 A | | 3/1997 | Clayman et al. |
| 5,619,763 A | * | 4/1997 | Randolph et al. ............... 5/601 |
| RE36,415 E | | 11/1999 | McKenna |
| 6,421,854 B1 | | 7/2002 | Heimbrock |
| 6,456,684 B1 | * | 9/2002 | Mun et al. ...................... 378/20 |

* cited by examiner

Primary Examiner—Craig E. Church
Assistant Examiner—Irakli Kiknadze
(74) Attorney, Agent, or Firm—McDermott Will & Emery LLP

(57) ABSTRACT

A patient table including a generally C-shaped lower base having opposing laterally extending end portions connected by a longitudinally extending central portion, and wherein the longitudinally extending portion is offset laterally from a longitudinally extending center line of the table. The table also includes an upper base, front and rear lift arms extending upwardly from the lower base and holding the upper base vertically above the lower base, and an elongated patient support pallet secured on one longitudinally extending side to the upper base and having an opposite longitudinally extending side substantially overhanging the laterally extending end portions of the lower base, and wherein the pallet is made of radiolucent material.

20 Claims, 6 Drawing Sheets

PATIENT TABLE WITH CANTILEVERED RADIOLUCENT PALLET

CROSS-REFERENCE TO RELATED APPLICATION

The present application claims priority from U.S. Provisional Patent Application Ser. No. 60/415,741 filed on Oct. 3, 2002, which is assigned to the assignee of the present application and incorporated herein by reference.

FIELD OF THE DISCLOSURE

The present disclosure relates generally to tomography systems and, more particularly, to a table for supporting a sample, such as a patient, in a tomography scanner during a scanning procedure. Even more particularly, the present disclosure relates to a patient table having a cantilevered, radiolucent pallet.

BACKGROUND OF THE DISCLOSURE

Medical diagnostic imaging and scanner systems such as magnetic resonance imaging (MRI) apparatus, X-ray machines, positron emission tomography (PET) scanners, and computer tomography (CT) scanners are well known. Such machines are quite popular as a tool for providing images of internal portions of patients for diagnosis of medical conditions, such as internal injuries, cancerous tumors and the like.

Some types of X-ray machines include an X-ray source and an X-ray detector mounted at opposite ends of a C-shaped arm. The C-shaped arm is often attached to a carriage which is displaceable in a horizontal, or longitudinal direction. The C-shaped arm is also rotatable about an axis extending along a center line of the C-shaped arm. The X-ray source and the X-ray detector can thus be adjusted in such a manner that the patient to be treated can be irradiated in all desired directions and from all desired positions. For example, the C-shaped arm is positioned around a portion of the patient sought to be imaged, such as a leg or arm, and then X-rays are directed at that portion of the patient by the X-ray source, pass through the body, and are received by the X-ray detector.

A factor affecting the quality of the acquired images is attenuation of the radiation between the source and the detector, which causes artifacts to be present in the resulting images. An artifact is any distortion or error in the image that is unrelated to the subject being studied. For X-ray CT, artifacts are any discrepancy between the CT numbers represented in the image and the expected CT number based on the linear attenuation coefficient. Artifacts degrade image quality as well as hide areas of pathology, so it is important to prevent them. Metallic objects, such as the metal frame of a patient table, are one cause of image artifacts.

In nuclear medicine, it is common to detect radiation by positioning the detectors at various different angles about the patient's body. Consequently, in certain instances, the table may be between a given detector and the patient's body, thereby causing attenuation of radiation reaching that detector and artifacts in the resulting image. Previous patient support tables provided basic support for the patient but also undesirably attenuated the radiation from the source to the detector. Additionally, some previous patient support tables require separate accessories for certain needs. Such accessories might include armrests, head support, etc.

What is still desired, therefore, is a new and improved patient support couch or table apparatus for use with medical diagnostic imaging and scanner systems. In particular, what is desired is a new and improved patient table which provides substantially unimpeded access for a C-shaped arm, X-ray source and X-ray detector of an imaging machine. What is also desired is a patient table with lowered attenuation that produces fewer and smaller image artifacts.

SUMMARY OF THE DISCLOSURE

The present disclosure provide a new and improved patient table. A patient table constructed in accordance with the present disclosure can be used for, but is not limited to, positioning a patient within a C-shaped arm and between an X-ray source and an X-ray detector of an imaging machine.

According to one exemplary embodiment of the present disclosure, the patient table includes a generally C-shaped lower base having opposing laterally extending end portions connected by a longitudinally extending central portion, and wherein the longitudinally extending portion is offset laterally from a longitudinally extending center line of the table. The table also includes an upper base, front and rear lift arms extending upwardly from the lower base and holding the upper base vertically above the lower base, and an elongated patient support pallet secured on one longitudinally extending side to the upper base and having an opposite longitudinally extending side substantially overhanging the laterally extending end portions of the lower base, and wherein the pallet is made of radiolucent material.

According to another exemplary embodiment of the present disclosure, the patient table is included as part of an X-ray system also including a C-shaped arm supporting at a first end an X-ray source for projecting a beam of X-rays to an X-ray detector supported on an opposite, second end of the C-shaped arm. The C-shaped arm can be moved longitudinally along the patient pallet of the table while one of the X-ray source and the X-ray detector is positioned over the pallet and the other of the X-ray source and the X-ray detector is positioned under the pallet.

The foregoing and other features and advantages of the present disclosure will become more readily apparent from the following detailed description of the disclosure, as illustrated in the accompanying drawing.

BRIEF DESCRIPTION OF THE DRAWINGS

Like reference characters designate identical or corresponding components and units throughout the several views.

DETAILED DESCRIPTION OF EXEMPLARY EMBODIMENTS

Figure 1:
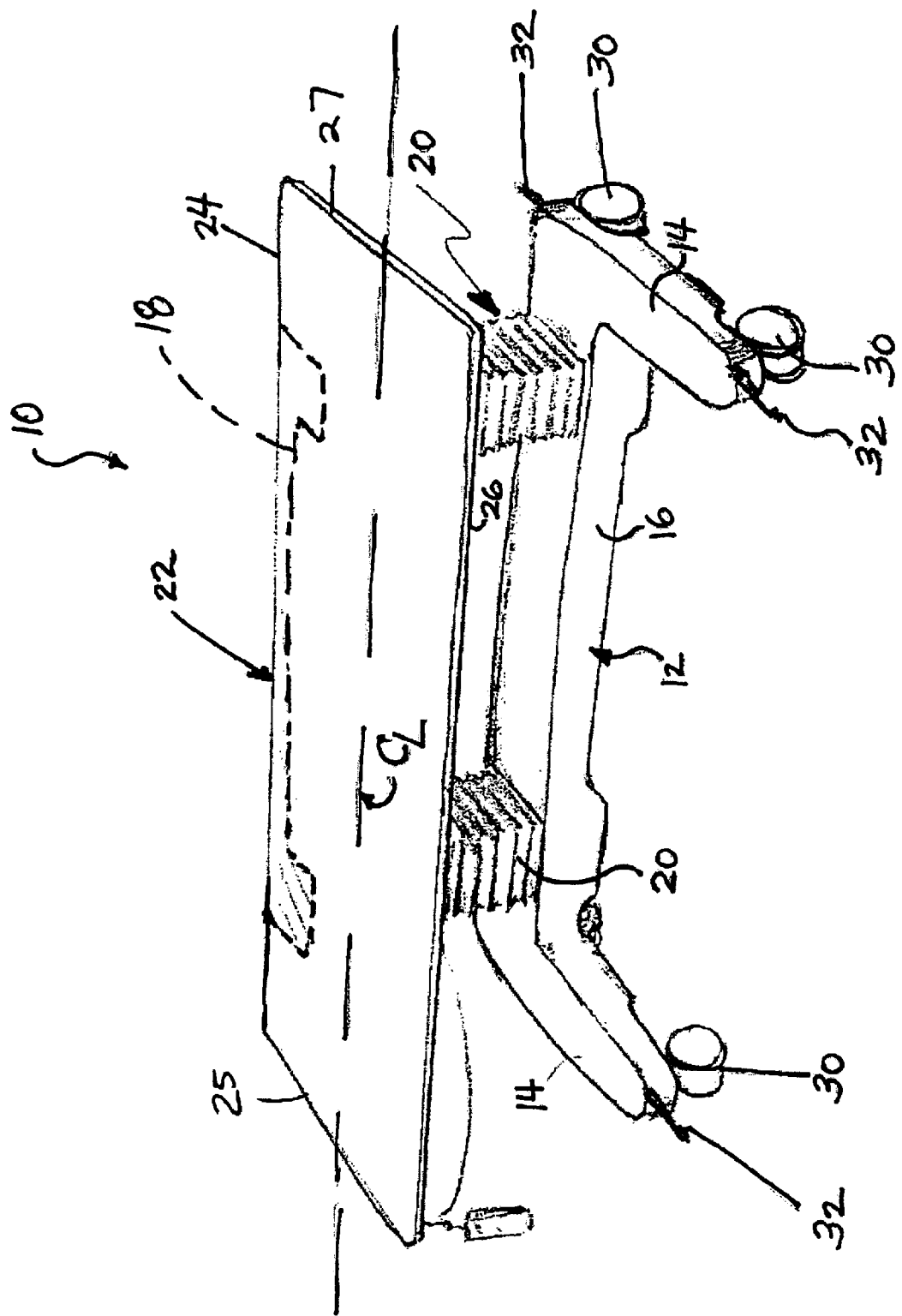
FIG. 1 is a top and side perspective view of an exemplary embodiment of a patient table constructed in accordance with the present disclosure.

Referring to FIGS. 1 through 8, an exemplary embodiment of a patient table 10 constructed in accordance with the present disclosure is shown. A patient table constructed in accordance with the present disclosure can be used for, but is not limited to, positioning a patient within a C-shaped arm 100 and between an X-ray source (not shown) and an X-ray detector 102 of an imaging machine, as shown for example in FIGS. 6 and 8.

The patient table 10 includes a generally C-shaped lower base 12 having opposing laterally extending end portions 14 connected by a longitudinally extending central portion 16, and wherein the longitudinally extending portion is offset laterally from a longitudinally extending center line of the table. The table 10 also includes an upper base 18, front and rear lift arms 20 extending upwardly from the central portion 16 of the lower base 12 and holding the upper base 18 vertically above the lower base, and an elongated patient support pallet 22 secured on one longitudinally extending side 24 to the upper base 18 and having an opposite longitudinally extending side 26 substantially overhanging the laterally extending end portions 14 of the lower base 12. The patient support pallet 22 also has opposing ends 25, 27 extending laterally between the sides 24, 26.

Figure 6:
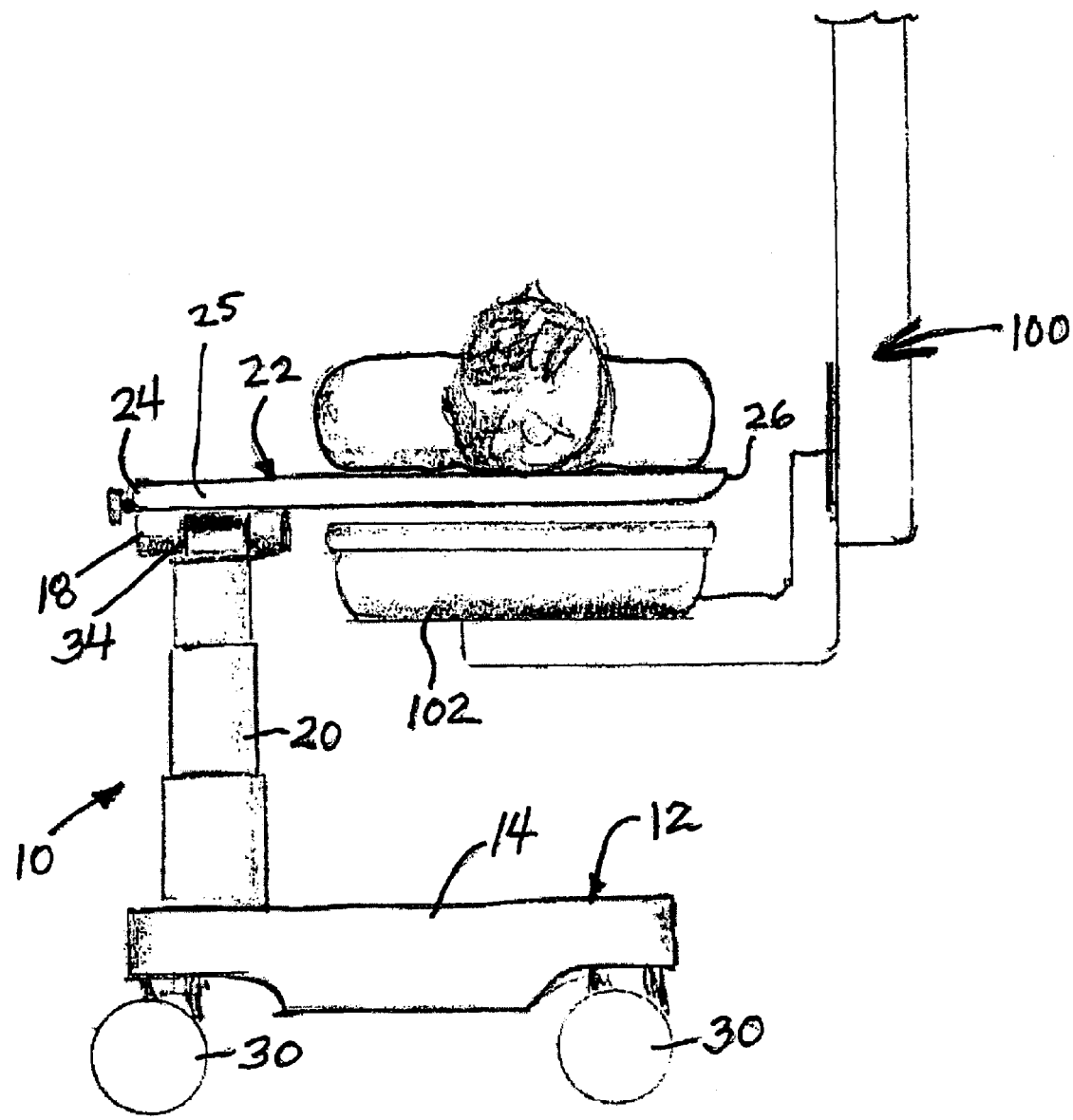
FIG. 6 is an end elevation view of the patient table of FIG. 1, wherein the table is shown in a fully raised position and wherein a patient is shown supported on a pallet of the table and an X-ray detector is positioned under the pallet.
Figure 7:
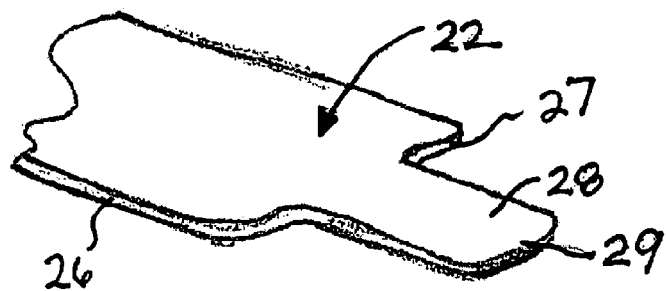
FIG. 7 is a perspective end view of a portion of the pallet of the patient table of FIG. 1.
Figure 8:
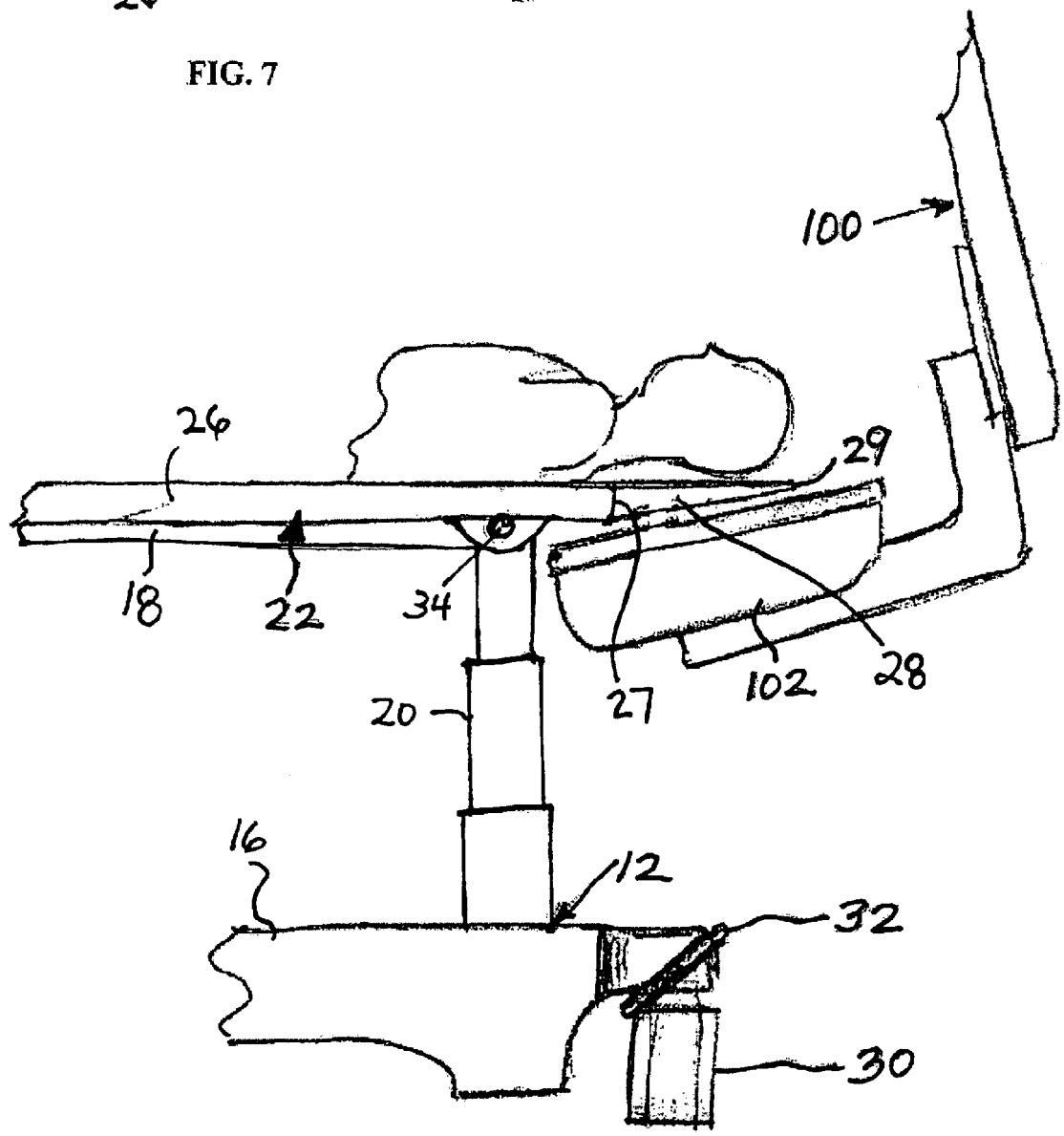
FIG. 8 is a side elevation view of the patient table of FIG. 1, wherein the table is shown in a fully raised position and wherein a patient is shown supported on the pallet of the table and an X-ray detector is positioned under the pallet.
Figure 10:
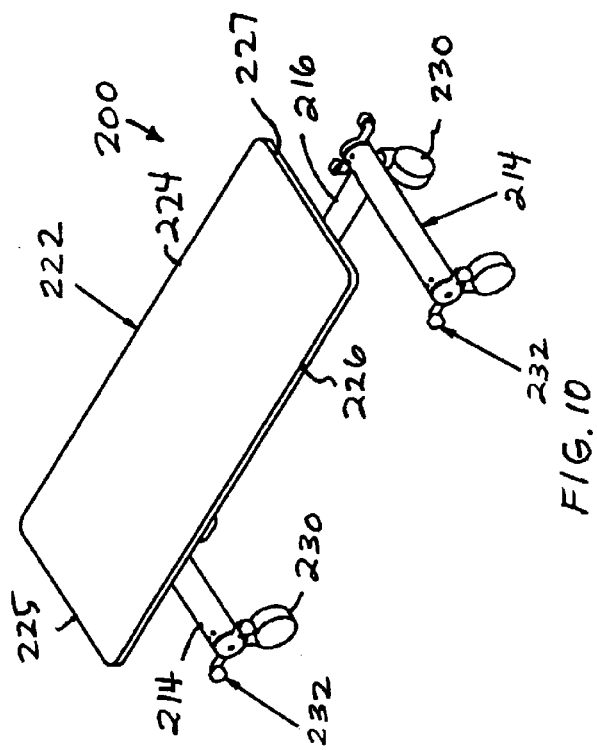
FIG. 10 is a top and side perspective view of the patient table of FIG. 9.

The elongated pallet 22 is shaped and sized for a patient to lie thereon, and is made from radiolucent carbon fiber surrounding a foam core, although other rigid radiolucent materials are acceptable. The table 10 is particularly suitable for use in endoscopy, cardiac catheterization, and other procedures requiring fluoroscopy. As shown in FIGS. 6 and 8, the table 10 is designed so that the C-shaped arm 100 of a fluoroscope machine can be moved longitudinally along the patient pallet 22 of the table 10 while one of the X-ray source and the X-ray detector 102 is positioned over the pallet 22 and a patient lying thereon, and the other of the X-ray source and the X-ray detector 102 is positioned under the pallet 22. As also shown in FIGS. 7 and 8, the pallet 22 can be provided with a narrow, extending head portion 28, and the pallet can also be provided with a cross-section that tapers towards an end 29 of the pallet to further accommodate the C-shaped arm 100 of a fluoroscope machine.

The patient pallet 22 contains no metal or other structure in three outside edges 25, 26, 27 that would produce artifacts in an X-ray picture. This allows patients to be imaged out to the edges 25, 26, 27 of the pallet 22, without artifacts caused by metal structure in the pallet 22 being present in the resulting images. The pallet 22 is also sufficiently wide (e.g., 30 inches) as to allow imaging of any part of the patient without repositioning of the patient on the pallet 22. In certain situations, shooting X-rays across the pallet 22, through the patient, and down below one of the three edges 25, 26, 27 of the pallet 22 is desired in order to obtain images of certain portions of the patient, such as images of a patient's hip joint. A patient table 10 constructed in accordance with the present disclosure allows such images to be produced without unwanted artifacts because the patient pallet 22 is made of radiolucent material and is unencumbered by metal support structure around three of its edges 25, 26, 27. As shown in FIG. 1, only one side 24 of the pallet 22 is encumbered by metal support structure, i.e., the upper base 18.

In the exemplary embodiment shown in FIGS. 1 through 6, the lower base 12 is supported by four tandem caster assemblies 30 to allow the patient table 10 to be rolled while supporting a patient (and also when not supporting a patient). Each caster assembly 30 is also provided with a manually operated foot brake and steering lock 32. The lower base 12 is made from a strong and rigid material, such as steel.

Figure 2:
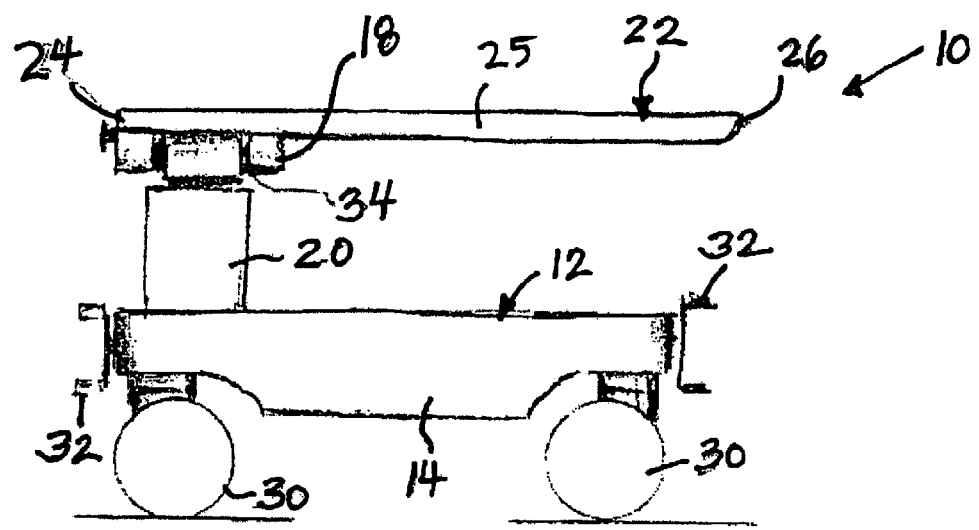
FIG. 2 is an end elevation view of the patient table of FIG. 1, wherein the table is shown in a fully lowered position.
Figure 3:
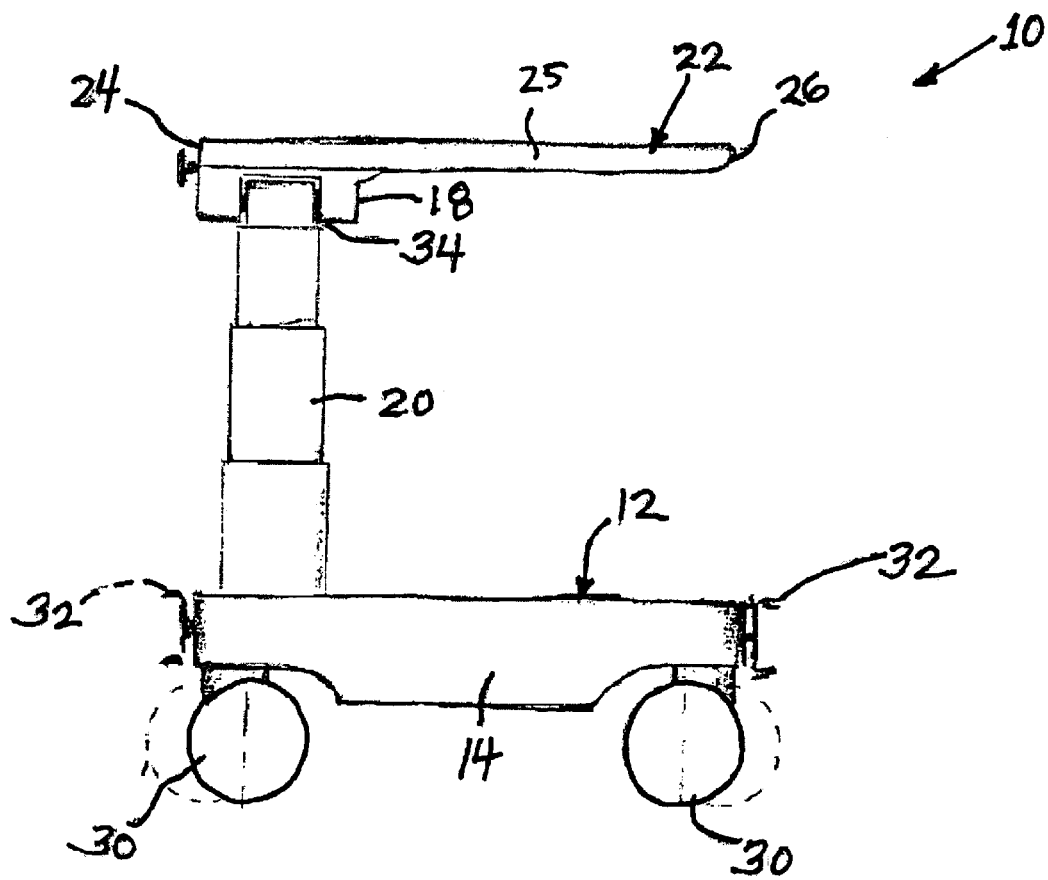
FIG. 3 is an end elevation view of the patient table of FIG. 1, wherein the table is shown in a fully raised position.

The upper base 18 is also made from a strong and rigid material, such as steel. In the exemplary embodiment shown, the lift arms comprise telescoping hydraulic cylinders 20 (which are shown covered by flexible boots in FIG. 1). The hydraulic cylinders 20 are spaced wide apart to provide room for maneuvering the C-Arm. The hydraulic cylinders 20 adjust the vertical position of the upper base 18 between a fully lowered position, as shown in FIG. 2, to facilitate patient egress and ingress, and a fully raised position, as shown in FIG. 3, to provide a comfortable position for a person, such as a doctor or nurse, standing next to a patient supported on the pallet 22. The hydraulic cylinders 20 are especially useful in lowering the patient pallet 22 to the level of a wheel chair, so that a person sitting in a wheel chair can simply drop an arm of the wheel chair and slide onto the patient pallet 22 of the lowered table.

Figure 4:
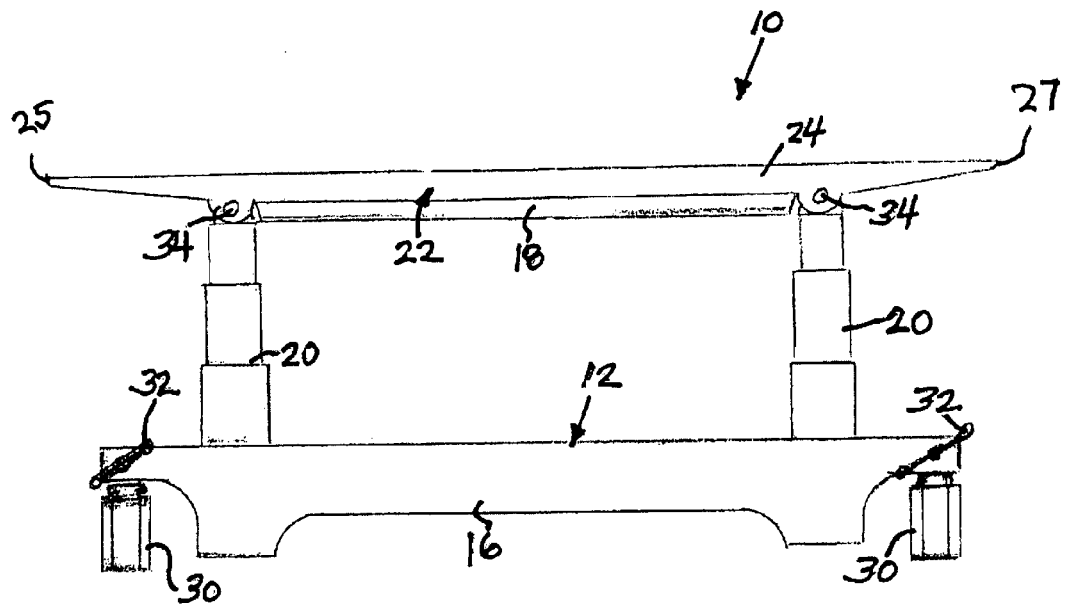
FIG. 4 is a side elevation view of the patient table of FIG. 1, wherein the table is shown in the fully raised position.
Figure 5:
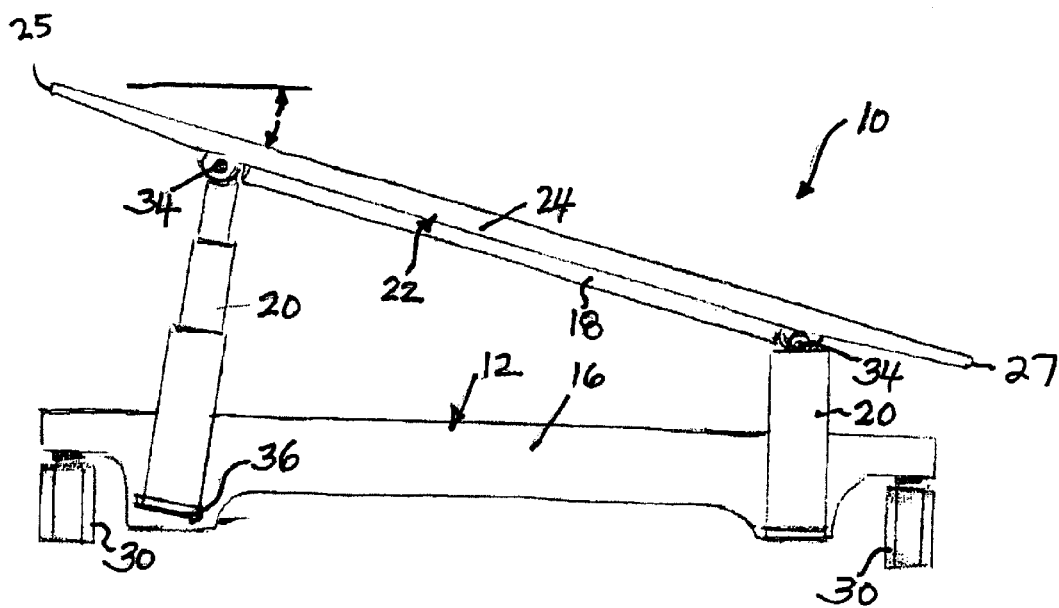
FIG. 5 is an opposite side elevation view of the patient table of FIG. 1, wherein one end of the table is shown in a fully raised position and an opposite end of the table is shown in a fully lowered position.

As shown in FIGS. 2 through 6, the hydraulic cylinders 20 are pivotally connected at hinges 34 to the upper base 18, and, as shown in FIG. 5, at least one of the hydraulic cylinders 20 is pivotally connected at a hinge 36 to the lower base 12. In this manner, the pallet 22 can be moved to one of two orientations: a flat, horizontal position as shown in FIG. 4, and a Trendelenburg position shown in FIG. 5, where a patient's feet are raised above the patient's head, or the patient's head is raised above the patient's feet.

The overall height of the patient table 10 in a fully lowered position may be selected to be about twenty inches, for example, such that no footstool is required for a patient to get on or off the pallet of the patient table. The overall height of the patient table 10 in a fully raised position may be selected to be about thirty-two inches, for example. In the fully raised position, it is preferably that there be at least twenty inches of vertical clearance between the lower base 12 and the pallet 22. The pallet 22 may be provided with a length of about eighty inches, for example, and a width of about twenty-six to thirty-two inches, for example. Preferably, there is provided a lateral clearance below the pallet 22 of at least twenty inches between the side 26 of the pallet and the lower base 14.

Another exemplary embodiment of a patient table 200 constructed in accordance with the present disclosure is shown FIGS. 9 through 12. The patient table of FIGS. 9 through 12 is similar to the patient table 10 of FIGS. 1 through 8 such that similar elements have the same reference numeral preceded by a "2".

Figure 12:
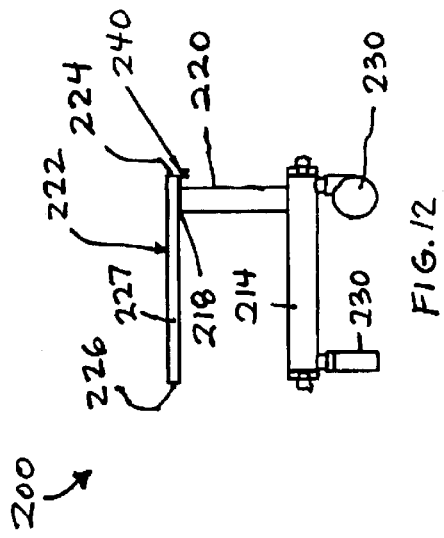
FIG. 12 is a side elevation view of the patient table of FIG. 9.
Figure 11:
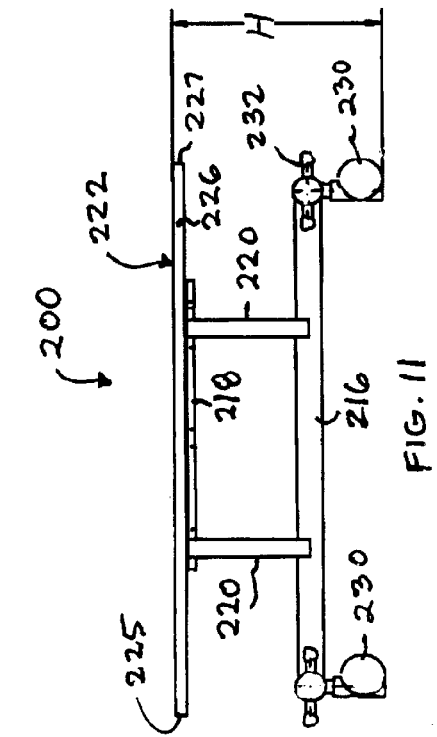
FIG. 11 is an end elevation view of the patient table of FIG. 9.

As shown best in FIGS. 11 and 12, the patient table 200 includes two lift arms 220, each of which has a fixed height (i.e., non-adjustable height). If desired, the table 200 can be provided with one lift arms 220, or more than two lift arms 220. As shown best in FIG. 11, the patient table 200 has an overall height "H". According to one exemplary embodiment, the height "H" is equal to about 28 inches.

Figure 9:
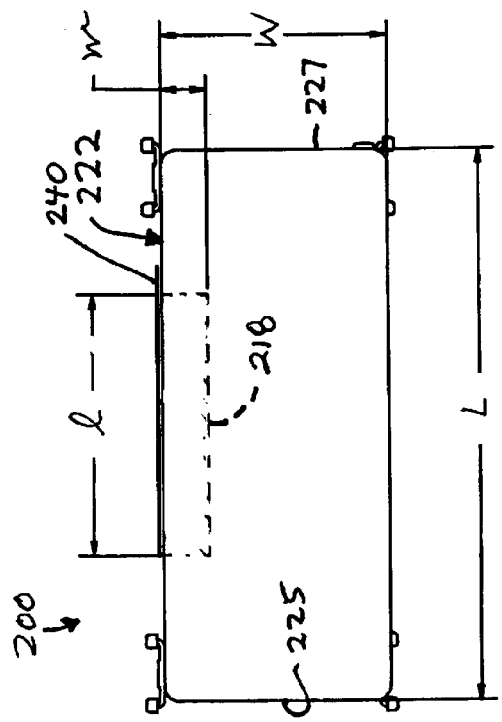
FIG. 9 is a top and side perspective view of another exemplary embodiment of a patient table constructed in accordance with the present disclosure.

As shown best in FIG. 9, the upper base 218 has a length "l" and a width "w", while the pallet 222 has a length "L" and a width "W". According to one exemplary embodiment, the upper base 218 has a length "l" equal to about 38 inches and a width "w" equal to about 6 inches, while the pallet 222 has a length "L" equal to about 80 inches and a width "W" equal to about 30 inches.

While patient tables constructed in accordance with the present disclosure are described and shown as being used with a fluoroscopy machine, the tables can also be used in other applications.

It should be understood that the embodiments of the present disclosure described herein are merely exemplary and that a person skilled in the art may make variations and modifications to the embodiments described without departing from the spirit and scope of the present disclosure. All such equivalent variations and modifications are intended to be included within the scope of these disclosure as defined by the appended claims.

What is claimed is:

1. A patient table having longitudinally extending center line and comprising:
   a lower base;
   an upper base;
   at least one lift arm extending upwardly from the lower base and holding the upper base vertically above the lower base, wherein the lift arm and the upper base are laterally offset from the longitudinally extending center line of the table; and
   an elongated patient support pallet made of radiolucent material and having opposing, longitudinally extending first and second sides extending parallel with the longitudinally extending center line of the table, wherein the first side of the pallet is secured to the upper base and the pallet is cantilevered from the upper base laterally across the center line of the table, so that the second side of the pallet is laterally offset from the center line opposite the upper base, whereby the lift arm and the upper base do not prevent a C-shaped arm supporting an X-ray source and an X-ray detector from being moved longitudinally alone a fall length of the patient pallet while one of the X-ray source and the X-ray detector is positioned over the pallet in alignment with the center line and the other of the X-ray source and the X-ray detector is positioned under the pallet in alignment with the center line.

2. An X-ray system including a patient table according to claim 1, and further comprising a C-shaped arm supporting at a first end an X-ray source for projecting a beam of X-rays to an X-ray detector on an opposite, second end of the C-shaped arm, wherein the C-shaped arm can be moved longitudinally along the patient pallet of the table while one of the X-ray source and the X-ray detector is positioned over the pallet and the other of the X-ray source and the X-ray detector is positioned under the pallet.

3. A patient table according to claim 1, wherein the pallet has an X-ray transparency equivalent to less than one millimeter of aluminum.

4. A patient table according to claim 1, wherein the lower base is supported by caster assemblies.

5. A patient table according to claim 4, wherein each caster assembly includes a manually operated foot brake and steering lock.

6. A patient table according to claim 1, wherein the lower base, the lift arm and the upper base are made of steel.

7. A patient table according to claim 1, wherein the lift arm has a fixed height.

8. A patient table according to claim 1, wherein the lift arm has an adjustable height.

9. A patient table according to claim 8, wherein the lift arm comprises a telescoping hydraulic cylinder.

10. A patient table according to claim 8, including two of the lift arms, wherein the lift arms are pivotally connected to the upper base.

11. A patient table according to claim 10, wherein at least one of the lift arms is pivotally connected to the lower base.

12. A patient table according to claim 1, wherein the lower base is generally C-shaped and includes opposing laterally extending end portions connected by a longitudinally extending central portion, wherein the longitudinally extending portion is offset laterally from a longitudinally extending center line of the table.

13. A patient table according to claim 12, including two of the lift arms.

14. A patient table according to claim 1, wherein the pallet is made of carbon fiber.

15. A patient table according to claim 1, wherein the pallet is made of carbon fiber surrounding a foam core.

16. A patient table according to claim 1, wherein the table has a height of about 28 inches.

17. A patient table according to claim 1, wherein the upper base has a length equal to about 38 inches and a width equal to about 6 inches, while the pallet has a length equal to about 80 inches and a width equal to about 30 inches.

18. A patient table according to claim 1, wherein a length of the upper base is less than a length of the pallet.

19. A patient table according to claim 1, wherein a width of the upper base is less than a width of the pallet.

20. A patient table according to claim 1, wherein opposing ends of the pallet each extend at least 20 inches longitudinally from the upper base, and the opposite longitudinally extending side of the pallet extends at least 20 inches laterally from the upper base.

* * * * *